United States Patent [19]

Byler

[11] 3,967,885
[45] July 6, 1976

[54] OPTICAL DEVICE FOR POST-OPERATIVE CATARACT PATIENTS

[75] Inventor: William H. Byler, Winter Park, Fla.

[73] Assignee: U.S. Radium Corporation, Morristown, N.J.

[22] Filed: Nov. 4, 1974

[21] Appl. No.: 520,647

[52] U.S. Cl. .................................................. 351/46
[51] Int. Cl.² ........................................... G02C 7/16
[58] Field of Search ............................... 351/45, 46

[56] References Cited
UNITED STATES PATENTS

| | | | |
|---|---|---|---|
| 1,959,915 | 5/1934 | Guthrie | 351/46 |
| 2,012,620 | 8/1935 | Bean et al. | 351/46 |
| 3,756,703 | 9/1973 | Nelson | 351/45 |

FOREIGN PATENTS OR APPLICATIONS

| | | | |
|---|---|---|---|
| 213,426 | 3/1958 | Australia | 351/45 |
| 398,850 | 6/1909 | France | 351/46 |
| 372,473 | 6/1907 | France | 351/46 |
| 472,390 | 9/1937 | United Kingdom | 351/46 |
| 1,026,839 | 4/1966 | United Kingdom | 351/46 |

OTHER PUBLICATIONS

*Popular Mechanics* advertisement, Nov. 1964.

*Primary Examiner*—Paul A. Sacher
*Attorney, Agent, or Firm*—Pennie & Edmonds

[57] ABSTRACT

An optical device for post-operative cataract patients comprising an opaque mask attached in spectacle frames or other means for mounting before the eyes. The mask includes an array of transparent areas, the size and positioning of which are interrelated to provide the eye with protection against excessive light and to increase the imaging and focusing capability of the eye.

27 Claims, 10 Drawing Figures

OPTICAL DEVICE FOR POST-OPERATIVE CATARACT PATIENTS

BACKGROUND OF THE INVENTION

Persons afflicted with cataracts in one or both eyes quite often must undergo surgery to remove the cataracts. A few days after such surgery, recovery is sufficient to allow use of the eye operated upon under restricted conditions. Since, however, the lens portion of the eye has been removed during surgery, the eye no longer has its primary focusing member and its focusing capability is only at a minimum compared to the normal eye. Without a lens, excessive light entering the eye becomes scattered which degrades contrast and clarity of vision. Excessive light can also cause damage to the unprotected eye while the eye is healing. Eventually, the patient will wear prescription lenses; but during the period immediately following surgery, the eye is in the process of healing and its focusing capability is undergoing change. Therefore, during this period, it is not feasible to obtain permanent glasses.

Temporary spectacles of various designs have, in the past, been made for the post-operative patient. Such spectacles have been designed in an attempt to permit limited activity of the patient and protection of the eye against damage due to excessive light. These prior constructions have, however, not proved satisfactory.

One type of temporary spectacles includes lenses molded from plastic. These molded lenses are less expensive than permanent glass or plastic lenses but are generally thick and uncomfortably heavy. They also have defects which cause disturbing image distortions and color distortions from chromatic aberrations. Lenses of this type are particularly disturbing when the wearer attempts to change his view from straight ahead to one side or the other where there is no lens at all. The presence of high powered lenses in front and none at the sides, as is the case with conventionally constructed glasses, creates a serious front to side transition. Objects at the side cannot be quickly focused to determine their proximity or direction of movement. For example, moving objects may appear to be at a safe distance when actually close and on a collision course.

Another type of post-operative spectacle presently available includes an opaque plate with a single aperture of about 2.5 mm. diameter. This type of spectacle has very poor acuity and a very narrow field of vision.

It has also been proposed to produce spectacles with an array of apertures of an apaque background but, to my knowledge, none would serve the purposes of this invention. These have been proposed for sufferers of myopia or for other limited purposes not related to lensless eyes. Constructions of this type are, for example, disclosed in U.S. Pat. Nos. 564,518 and 1,959,915. They would be unsatisfactory for use by post-operative cataract patients in that they either would not provide adequate imaging, would permit excessive light to enter the lensless eye, would not provide a sufficient field of vision or sufficient light, would require a glass lens as a primary optical device, or would have a combination of these defects.

SUMMARY OF THE PRESENT INVENTION

In accordance with the teachings of applicant's invention, one form of the optical device is comprised of an opaque plate with a centrally located array of small transparent areas, the array area occupying about 40% of the total plate area. One or two of these plates may be used depending on whether one or both eyes have been operated upon. These transparent areas are of a size having a diameter ranging from 0.375 mm. to 0.8 mm. They are formed in linear rows with their centers spaced between 2.0 mm. and 5.5 mm. apart. With this construction the lensless eye is capable of receiving light in sufficient, yet restricted, quantity so as to permit adequate imaging for the convalescing patient. In this preferred construction, transparency of the entire plate is less than 0.5% and transparency of the array portion is only 1.23%. Also, the field of vision is sufficient to permit good mobility.

In another form of the invention, the optical device is of wrap-around construction; that is, it extends beyond the side edges of the normal flat type of eyeglass lens and back to the wearer's temples. With this construction, the array of transparent areas will extend in a curved path to the sides of the individual's eyes to provide imaging capabilities through a 180° field of vision. Also, with this construction, a lens of moderate power, for example, 2 to 6 diopters, may be added to the front of the device. In combination with the side array of transparent areas, this will significantly improve front vision acuity where it is most needed and yet avoid the front to side transistion problem normally present with conventional cataract lenses due to the radical difference in optical power from front to side. In the wrap-around apertured construction, the arrays to the sides of the individual's eyes substantially reduces this power difference. The wrap-around construction advantageously also has a curved bottom edge extending to the individual's cheeks and the array of transparent areas follows this curve to improve imaging and focusing immediately in front of the wearer.

DETAILED DESCRIPTIONS OF THE PREFERRED EMBODIMENTS

Figure 1:
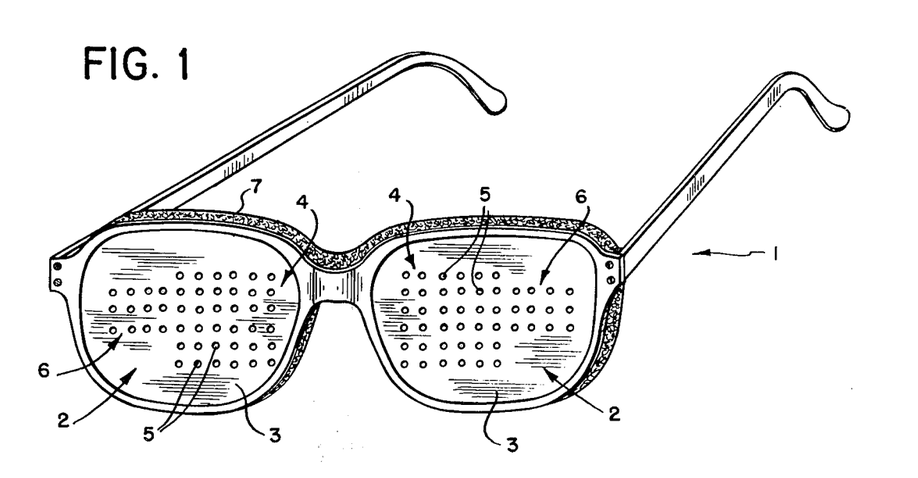
FIG. 1 is a view of a pair of eyeglass frames incorporating two of the optical devices of the present invention.

In FIG. 1 a pair of eye glass frames 1 is shown as incorporating the optical device 2 of the present invention, one device being provided for each eye. Two optical devices would be used in a situation where the cataract sufferer has undergone removal of the cataracts in both eyes.

In construction the optical device is fabricated from an opaque material, such as photographic film or sheet metal, which can be cut into a mask or plate 3 for fitting into eyeglass frames or other means for mounting before the eyes. Disposed on the opaque plate is a central array 4 of the transparent areas 5. Advantageously, these areas are circular transparent openings in the plate through which the patient's eye will focus. In accordance with the teachings of the present invention, the size, spacing and overall pattern of the array of transparent areas is important.

In the construction shown in FIG. 1 the plate has a size of about 40 × 50 mm. which is a conventional size of an eyeglass lens. The central array 4 of transparent areas is located centrally of the mask or plate and forms a square pattern of 21 mm. to a side. The transparent areas 5 which define the array are spaced on centers 4 mm. apart. Such a construction provides six horizontal and six vertical, linear rows of transparent areas in parallelogram pattern. The diameter of each of the transparent areas in the construction of FIG. 1 is 0.5 mm.

To increase the peripheral vision of the eye, a side array 6 of transparent areas 5 is provided. This side array extends horizontally from the central array 4 toward the outside of the frames. In the construction shown in FIG. 1, the side array is disposed adjacent the top of the array 4 and has the vertical height of 9 mm. and horizontal length of 17 mm. With transparent areas extending in this direction, the patient's capability of viewing objects located to his side is increased. This is desirable if the patient, as usual, intends to walk during the convalescing period.

To prevent extraneous light from entering the eye from the side, the eyeglass frames 1 are provided with a foam plastic cushion 7. This cushion is positioned about the periphery of the lens holding sections of the eyeglass frames and is adapted to fit snugly against the patient. With this construction, the only light entering the patient's eye will be through the transparent areas 5.

In the construction of the optical device as described above and shown in FIG. 1, the size, spacing and pattern formed by the array of transparent areas restricts excessive light from entering the healing eye and thus prevents injury to the eye. Also, the construction of FIG. 1 provides a substantial reduction in scattered light which can cause degradation of contrast. Although the size of the transparent areas restricts extraneous light from entering the eye, there areas are formed to a dimension which produces sufficient focusing or imaging power to compensate for the removed lens at least to the extent of permitting limited clear vision. The array of transparent areas shown in FIG. 1 also permits a sufficient field of vision to enable the patient to walk around without fear of stumbling or falling over some unseen obstacle.

Limited variations in the dimension of the pattern formed by the array of transparent areas, the size of the areas and their spacing can be made without losing the protective and focusing capabilities of the device. For example, it is contemplated that the size of the transparent areas may vary from 0.375 mm. to 1.0 mm. in a diameter with 0.65 mm. being preferred. Sizes smaller than this make the field of view too dark for good mobility and tend toward loss of clear imaging due to edge distortion; sizes larger than this do not provide acceptable focusing. The transparent areas are advantageously oriented in linear rows on a parallelogram pattern. These may be arranged so that the transparent areas form a square or rectangular pattern or, for example, a hexagonal pattern by staggering rows. Another dimension of the construction shown in FIG. 1 which can vary is the spacing between the transparent areas 5. In particular, these areas may be formed on centers spaced from each other by 2.0 mm. to 5.5 mm. with 4.0 mm. being preferred. The exact spacing which is used will depend partly on the dimension of the transparent areas and relates primarily to the desirability of minimizing awareness of the pattern by the user. Generally, each of these dimensions is interrelated with the others; and changing of one requires changing of one or more of the others in order to produce a device having the desired protective and focusing capabilities uniquely required by cataract patients.

Figure 10:
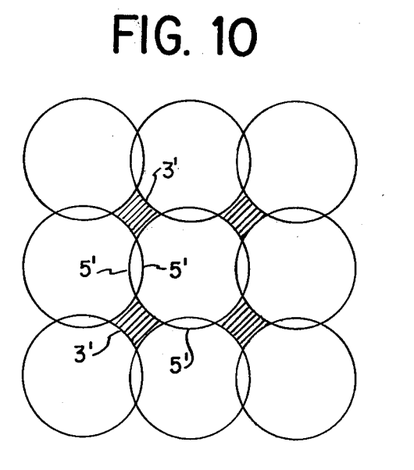
FIG. 10 is a schematic drawing showing the apparent optical viewing pattern formed by the optical device of the present invention.

FIG. 10 shows the relationship between the size of the transparent areas and their spacing as one with normal sight would see it when placed before the eyes in the normal position of use. With a construction wherein the transparent areas are circular with a diameter of 0.65 mm. and a center to center spacing of 4.0 mm., the individual circular areas will appear to overlap slightly when the device is placed before the individual's eye. This overlapping is shown in FIG. 10 by the lines 5'. When the device is placed before the individual's eye, the opaque mask or plate 3 tends to disappear and is seen only as small diamond shape areas 3'.

In determining the size and spacing of the transparent areas of the arrays, it has been found that if the diameter of the areas is chosen to be at the lower end of the range of 0.375 to 1.0 mm. and the spacing of the areas is chosen to be at the upper end of the range of 2 to 5.5 mm., the apparent pattern which is formed will show objectionable break-up. In other words, the individual transparent areas will appear to be separated from each other and a larger portion of the mask will block the individual's sight. If, on the other hand, the diameter of the transparent areas is at the larger end of the range and the spacing is at the smaller end, objectionable overlapping of the transparent areas will be formed. This will admit too much light through the optical device. Thus, in choosing the diameter and spacing of the transparent areas from the ranges given above, these two dimensions are considered together so that the transparent areas create a pattern with an apparent slight overlap of each area with the next adjacent areas both above and below and to each side.

Figure 2:
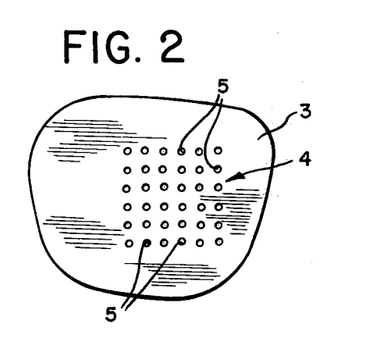
FIG. 2 is a view of a modified embodiment of the optical device shown in FIG. 1.

FIG. 2 shows a modified embodiment of the optical device of FIG. 1 wherein the arrays 6 are omitted leaving only the central arrays 4. The square patterns formed by the arrays 4 shown in FIG. 2 are the same as the central arrays 4 of the embodiment of FIG. 1. Variations of the patterns discussed with respect to the embodiment of FIG. 1 apply equally with that of FIG. 2.

Figure 3:
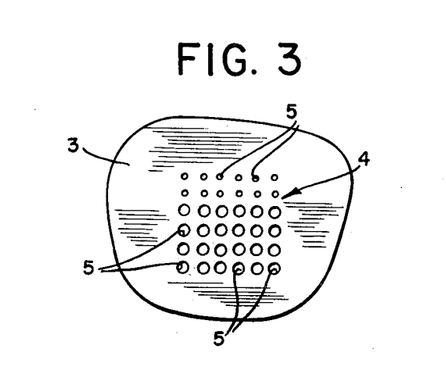
FIG. 3 is a view of still another modified embodiment of the optical device in FIG. 1.

FIG. 3 shows another modified embodiment of the optical device in which the upper two rows of transparent areas 5 are formed with diameters of 0.4 mm. The remaining rows are formed with diameters of 0.7 mm. A construction like that shown in FIG. 3 will provide more restriction of ambient light from above where it is most likely to come from. Also, with the smaller transparent areas in the upper rows, added acuity is provided when looking through these areas. This is advantageous where the patient desires to read or do paper work. The increased size of the lower transparent areas provides less sharply focused but more brightly lighted observation of the area viewed through these openings.

Although one particular arrangement of transparent areas and sizes is shown in FIG. 3, variationsn can be made along the lines discussed above with respect to the construction shown in FIG. 1. Particularly, the diameter of the upper smaller transparent areas may range from 0.375 mm. to 0.45 mm. while the diameter of the larger areas at the bottom of the array may vary from 0.45 to 0.7 mm. Also, the number of smaller rows may be increased depending on the specific purposes for which the device is to be used.

Figure 4:
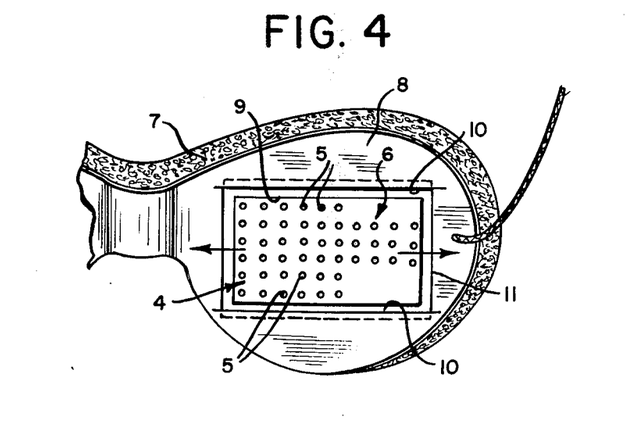
FIG. 4 is a view of the optical device showing an adjustable construction.

In order to facilitate use of the optical device of the present invention by different patients, it is necessary that the array over at least one of the eyes be adjustable in a horizontal direction. This is needed so that the arrays can be centered with respect to the individual's eyes. A construction for facilitating adjustment of the array in front of one of the patient's eyes is shown in FIG. 4. Here the optical device includes an opaque member 8 having a central opening 9 in front of the eye. Horizontal slits 10 are formed above and below the opening. The desired array 4, 6 or 4 is formed on an insert member 11 which is mounted on the member 8 by inserting the opposite edges into the slits 10. It is to be noted that the length of the slits 10 is greater than the width of the insert 11. The amount of adjustability provided for is about equal to one-half the distance between the transparent areas. Thus the insert may be shifted laterally to center it with respect to the individual's eye.

In addition to providing for horizontal adjustment, the slits 10 permit the plates to be adjusted vertically. By positioning the array in front of one eye out of horizontal alignment with the array in front of the other eye, the distraction one might feel because of the array pattern is reduced. With the preferred transparent area diameter of 0.65 mm. and a spacing of 4.0 mm., shifting of one array vertically with respect to the other array so that they are out of horizontal alignment by about 1 mm. has been found to be suitable for this purpose.

In FIGS. 5–9, the wrap-around embodiment of the optical device of the present invention is shown. The wrap-around construction has the advantage of permitting continuation of the transparent array around to the sides of the individual's eyes to provide, in effect, a 180° plus field of vision, the same field of one with normal eyes. The advantages of this construction are that it permits the patient to focus not only on objects in his forward line of sight but on objects to either side. This can sometimes be extremely important as, for example, where an object is approaching the individual from the side. Without any focusing power to the side, the individual cannot appreciate the nearness of the object or its path of approach. Not only is this the situation with post-operative cataract patients wearing the optical device of the present invention as shown in FIGS. 1–4, it is even more true with post-operative patients who are wearing cataract lenses. These lenses are usually high powered as, for example 12 diopters. When a patient views an object through such lenses, his eyes obviously become accustomed to the lenses. If he attempts to turn his eyes to the side where he has no focusing power, there is a tremendous front to side transition of focusing.

Figure 8:
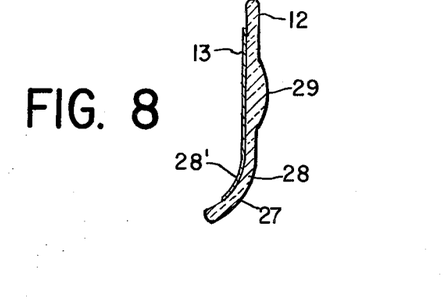
FIG. 8 is a cross-sectional view of a modified construction of the embodiment of FIG. 5.

With the wrap-around construction of applicant's invention, the continuation of the arrays to the sides of the individual's eyes removes this transition problem and the patient is provided with equal focusing power to the front and to the sides. In addition, it is possible to add a lens of moderate power as, for example, 2–6 diopters, to the front section of the wrap-around construction. Such a modification is shown in FIG. 8 and will be described in detail below. Generally, it is advantageous in that it permits added focusing power in front of the individual; and in combination with the transparent arrays to the sides, lessens the transition problem when changing one's view from front to side.

The wrap-around construction of the present invention also provides physical protection. The entire structure acts like a bandage protecting the individual's eyes from wind and dust. Also, with the wrap-around construction with the side arrays, light entering the side apertures is less effective toward diminishing contrast than light entering the eye through the front apertures. Thus, the side arrays enhance imaging while adding physical protection and light shielding without sacrificing anything significant.

Figure 5:
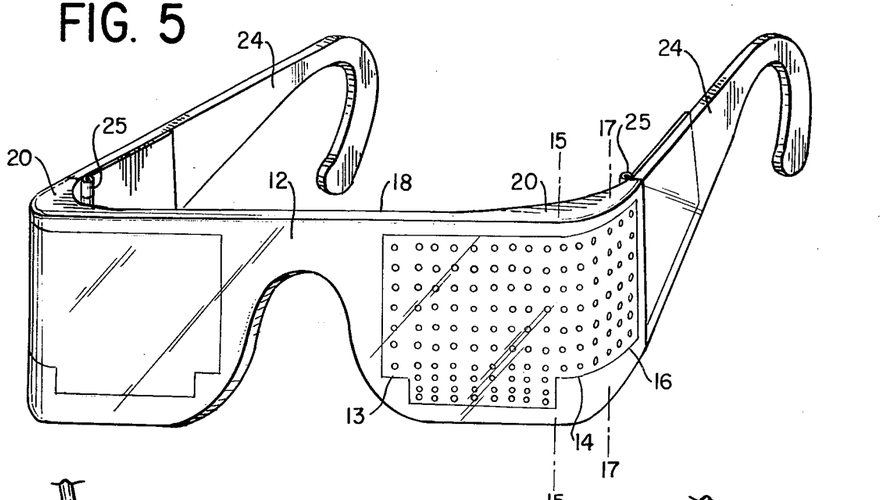
FIG. 5 is a perspective view of a wrap-aroound form of the optical device of the present invention.
Figure 6:
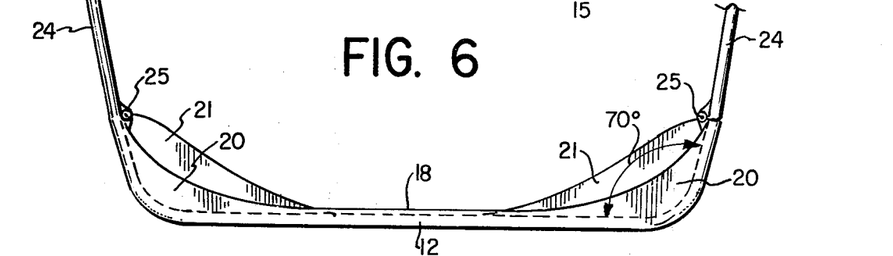
FIG. 6 is a top view of the embodiment shown in FIG. 5.
Figure 7:
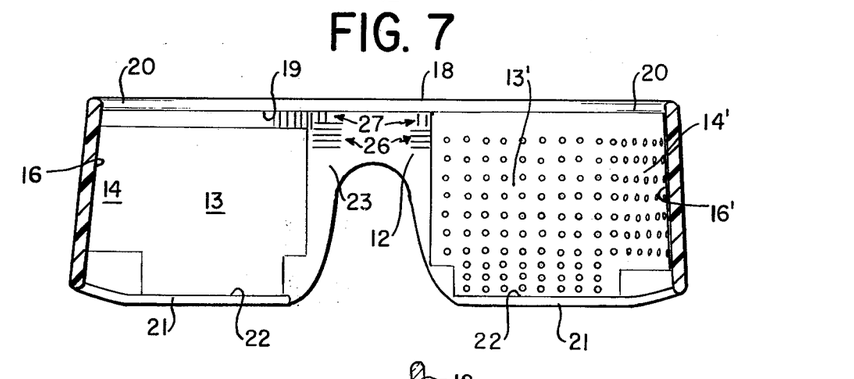
FIG. 7 is a back view showing the inside of the device shown of FIG. 5 with one of the masks removed.

FIGS. 5–7 show one construction of the wrap-around optical device of the present invention. As there shown, the device includes a frame structure 12 which is generally flat in front and curved along the outsides. The frame structure is opaque and is provided with a clear window area for mounting the apertured optical device. FIG. 7 shows the construction with one mask removed to expose the window area.

A window area is disposed to each side of the center of the frame structure and each window area includes a first front section 13 which is generally flat in shape. In the preferred construction, the front window section has a height of 37 mm. and a width of 37 mm. The window area also includes a second curved section 14. This section is curved about a vertical axis, as cnsidered when the frame structure is on the individual's face, and extends from the outside edge of the front section through the arc of about 70° and over a distance of about 10 mm. The outside edge of the front section is indicated by dashed line 15—15. The height of the window area in the second section is 28 mm. with the top edge forming a continuation of the top edge of the window area in the first section. The window area further includes a third generally flat section 16 extending beyond the curved section and having a height of 28 mm. and a width of 20 mm. The boundary between the second and third sections is shown in FIG. 5 by the dashed line 17—17.

For the wrap-around construction, the optical device includes a mask or plate with a primary and secondary array of transparent areas formed therein. In the preferred construction, the primary area includes transparent areas of a diameter of 0.65 mm. with a center to center spacing of 4.0 mm. As shown in the right-hand side of FIG. 7, the mask includes a first front section 13', second curved section 14' and a third side section 16'. These sections of the mask generally overlie the corresponding sections of the window area. The primary array of transparent areas covers most of the first front section of the mask and all of the second and third sections. More particularly, the primary array includes 9 vertical columns and 7 horizontal rows of transparent areas in the front section of the mask. These are shown in FIG. 7 as the first 7 top rows. In the second and third sections of the mask, an additional 6 vertical columns and 7 horizontal rows of transparent areas are provided. These rows form the continuation of the top 7 rows in the front section of the mask; and together, all of these transparent areas define the primary array.

In addition to the primary array, the wrap-around construction includes a secondary array disposed in the front section of the mask at the bottom of the primary array. This secondary array is shown in FIG. 7 as including 8 columns of transparent areas in 3 horizontal rows. The spacing of the transparent areas in the secondary array is smaller than in the primary array. In particular, the vertical spacing is preferably 2.5 mm. rather than 4.0 mm. The horizontal spacing, however, remains the same as does the size of the apertures, although it is within the scope of this invention to increase the size of these lower transparent areas similar to the manner shown in FIG. 3.

The mask or plate containing the transparent array can, as indicated above, be constructed of plastic film or thin metal. Photographic film is well suited for this purpose and permits formation of the transparent areas by photographic means. Also, the film construction provides a solid protective barrier for the eye and is easy to clean. As an alternative, a thin apertured film or metal may be used. The advantage of an apertured construction is that the thin aperture edges aid acuity and focusing.

In order to secure the masks to the frame structure and to align the masks with respect to each other, guide means are provided on the frame structure. As shown in FIGS. 6 and 7, the guide means includes a raised rib 18 extending along the top inside part of the frame structure. This rib provides a lower edge 19 which is adapted to be engaged by either one of the masks for alignment purposes. The raised rib also functions as a barrier against entering of light between the frame structure and the individual's face. For this purpose, the rib has a thickness which substantially fills the space normally present between conventional eyeless frames and the individual's face. As shown in FIG. 6, the rib is thickest at the curved sections 20.

In addition to the rib 18 there is a further rib 21 at the bottom of the frame structure. This rib has an upper surface 22 adapted to engage the lower edges of the masks for alignment purposes. The rib 21 also has a thickness to fill the opening between the frame structure and the individual's cheeks so as to thereby act as a light barrier.

In addition to the ribs 18 and 21, the frame structure is provided with light guards 23 along the nose part. Additional light barrier structure can be provided where necessary so that all light entering the individual's eyes will be restricted to passing through the apertures as is the case with the construction shown in FIG. 1.

The frame structure shown in FIG. 5 is completed by the temple pieces 24. These temple pieces are flexibly attached to the frame structure as shown at 25.

In mounting the masks onto the frame structure, the guide ribs are used to effect vertical positioning. As indicated above, it is advantageous to position one of the masks with its array slightly out of horizontal alignment with the array of the other mask. To facilitate this, millimeter graduated markings 26 are provided on the inside of the frame structure. Additional graduated markings are provided at 27 so that the horizontal spacing of the two arrays may also be adjusted to accommodate the individual.

Once the masks are in position they can be secured by tape or other suitable means. Taping permits ready removal of the masks and replacement with other masks having different patterns and arrays. This is advantageous in that one array permitting the entrance of more light may be found suitable for nighttime use whereas an array with more restricted light admission would be suitable for daylight use in brightly lighted areas. Of course, the array that is chosen will have to meet the same criteria as discussed above with reference to FIG. 10. In this regard, it is to be noted that the ranges of size and spacing of the array with the wrap-around construction is the same as with the flat construction of FIGS. 1–4.

A modified construction of the wrap-around embodiment of the invention is shown in FIG. 8. Here the frame structure 12 is shown as having a curved section 27 at the bottom. This curved construction provides for a fourth bottom window section 28 curved to the shape shown in FIG. 8 and extending from the bottom edge of the first window section 13. The curve of the frame structure extends to the individual's cheek and provides a light blocking effect. The mask to be attached to the frame structure of the construction shown in FIG. 8 has a fourth bottom section 28' overlying the window section 28. The secondary array of transparent areas continues into this fourth section. IN particular, the array in this section of the mask includes 8 columns and 3 additional rows of transparent areas. This construction enhances the focusing and imaging capabilities of the device in the area immediately in front of the patient.

As also shown in FIG. 8, the optical device of the present invention can include a lens 29 for increasing the focusing power directly in front of the individual. As previously indicated, this lens in combination with the side arrays of transparent areas increases the individual's ability to focus quickly on objects in front and to his side. This can be done with a moderate power lens as, for example, one having a power of between 2–6 diopters. In construction, the lens is a plano-convex lens having a diameter of 30 mm. and a thickness of 1 mm. Preferably, it is molded as part of the window structure of the optical device. Alternatively, it may be provided as a clip-on construction. With the molded lens as shown in FIG. 8, the convex surface of the lens is on the front surface of the window so as not to interfere with the surface mounting area for the masks which are mounted on the inside surface of the window area.

Figure 9:
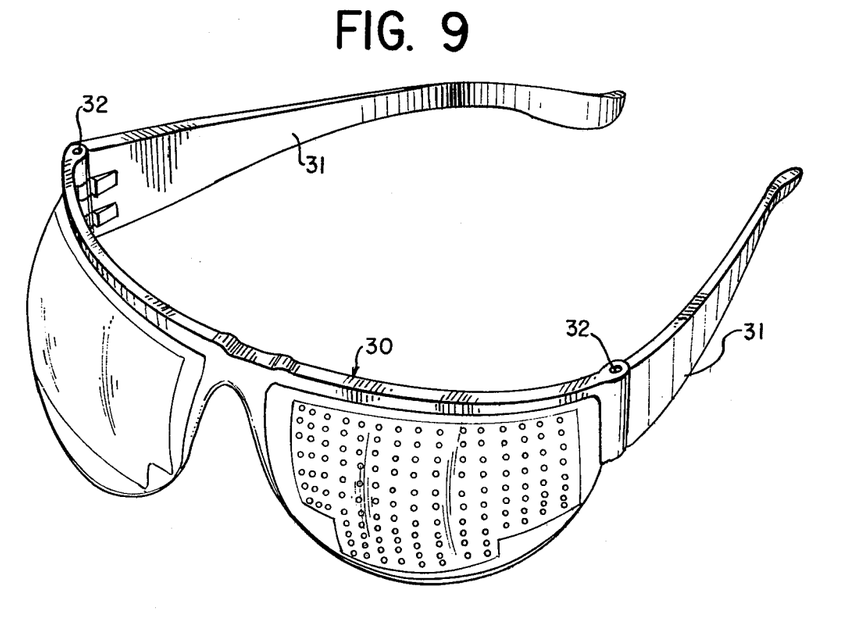
FIG. 9 is a perspective view of still another modified embodiment of the wrap-around construction of the optical device of the present invention.

Another embodiment of the wrap-around construction is shown in FIG. 9. This construction is advantageously made of plastic with a front part 30 molded to provide both the front, curved, side and bottom window sections corresponding to the four window sections of the embodiment shown in FIG. 5. Temple pieces 31 are provided and hinged at 32. The pattern of transparent arrays in this embodiment will conform to the limitations discussed above. Masks used with this construction will be attached to the inside surface of the front part 30. Alternatively, the window sections may be coated with opaque material with the aperture array patterns formed thereon. Plastic glasses of this construction may be bought as a conventional item and the masks of the present invention quickly formed on or attached thereto.

I claim:

1. An optical device for use by post-operative cataract patients in combination with means for holding the device in position before the eye, saidd optical device comprising:
   a. an opaque mask for mounting before the eye, said mask having:
      1. a first front section for disposition generally in front of the eye in the line of sight of forward vision,
      2. a second curved section extending from the outside edge of the front section in a generally curved pattern for disposition to the side of the individual's eye, and
      3. a third side section extending from the second curved section toward the individual's temple when the mask is positioned before the eye; and
   b. an array of discrete circular transparent areas on said mask:
      1. said array extending along the surface area of each of the sections of said mask, and
      2. said transparent areas being of a size and formed on centers spaced from each other in a pattern providing imaging for the eye when viewing objects through each of the sections of the mask.

2. An optical device according to claim 1 wherein:
   a. said array covers a major part of the surface area of the sections of said mask.

3. An optical device for use by post-operative cataract patients in combination with means for holding the device in position before the eye, said optical device comprising:
   a. an opaque mask for mounting before the eye, said mask having:
      1. a first front section for disposition generally in front of the eye in the line of sight of forward vision,
      2. a second curved section extending from the outside edge of the front section in a generally curved pattern for disposition to the side of the individual's eye, and
      3. a third side section extending from the second curved section toward the individual's temple when the mask is positioned before the eye; and
   b. an array of discrete circular transparent areas on said mask;
      1. said array extending along the surface area of each of the sections of said mask, and
      2. said transparent areas being of a size and spaced from each other in linear rows in parallelogram pattern, the size and spacing of the areas generally creating an apparent slight overlap of each area with the next adjacent areas above and below and to each side when the mask is positioned before the eye to provide imaging for the eye.

4. An optical device according to claim 3 wherein:
   a. the mask includes a fourth bottom section extending from the bottom edge of the first front section in a generally curved pattern for disposition below the individual's eye and extending to the individual's cheek when the mask is positioned before the eye; and
   b. said array extends along the surface area of said fourth section.

5. An optical device according to claim 3 wherein:
   a. the array on the front, curved and side sections of the mask includes a primary array of transparent areas each having equal diameters of between about 0.375 and 1.0 mm. and located on centers spaced equally from each other from between about 2.0 to 5.5 mm.

6. An optical device according to claim 5 further including:
   a. an optical lens disposed at about the center of said front section, said lens having a moderate power of between about 2 and 6 diopters.

7. An optical device according to claim 5 wherein:
   a. the primary array on the front, curved and side sections is defined by transparent areas having diameters of about 0.65 mm. and center to center spacings of about 4 mm.

8. An optical device according to claim 7 wherein:
   a. the array on the front section further includes a secondary array of transparent areas at the bottom of the primary array with horizontal center to center spacing of about 4 mm. and vertical center to center spacing of about 2.5 mm.

9. An optical device according to claim 8 wherein:
   a. the primary array is defined by about 15 vertical columns of transparent areas and about 7 horizontal rows; and
   b. the secondary array is defined by about 8 vertical columns of transparent areas and about 3 horizontal rows.

10. An optical device according to claim 8 further comprising:
    a. an optical lens disposed at about the center of said front section, said lens being a plano-convex lens about 30 mm. in diameter and about 1 mm. in thickness and having a moderate power of from about 2 to 6 diopters.

11. An optical device according to claim 9 wherein:
    a. the mask includes a fourth bottom section extending from the bottom edge of the front section in a generally curved pattern for disposition below the individual's eye and extending to the individual's cheek when the mask is positioned before the eye; and
    b. the secondary array of transparent areas further includes about 3 horizontal rows of transparent areas along the fourth section of the mask.

12. An optical device for use by post-operative cataract patients in combination with means for holding the device in position before the eye, comprising:
    a. an opaque mask for mounting before the eye, said mask having:
       1. a first front section for disposition generally in front of the eye in the line of sight of forward vision,
       2. a second curved section extending from the outside edge of the front section in a generally curved pattern for disposition to the side of the individual's eye, and
       3. A third side section extending from the second curved section toward the individual's temple when the mask is positioned before the eye;
    b. an array of discrete circular transparent areas on said mask:
       1. said array extending along the surface area of the sections of said mask,
       2. said transparent areas being of a size and spaced from each other in linear rows in parallelogram pattern, the size and spacing of the areas generally creating an apparent slight overlap of each area with the next adjacent areas above and below and to each side when the mask is positioned before the eye to provide imaging for the eye, and 3. the array on the front, curved and side sections of the mask including a primary array of transparent areas each having equal diameters of between about 0.375 and 1.0mm. and located on centers spaced equally from each other from between about 2.0 to 5.5mm.;

c. an opaque eyeglass frame structure;

d. a clear window area within the frame structure for disposition in front of and to the side of each of the individual's eyes, each of said window areas having:

1. a first flat front section having a height of about 37 mm. and a width of about 57 mm., 2. a second section curved about a vertical axis and extending from the outside edge of the first front section through an arc of about 70° and over a distance of about 10 mm. and having a height of about 28 mm. with the top edge of the second section forming a continuation of the top edge of the first section, and 3. a third flat section extending from the curved section and having a height of about 28 mm. and a width of about 22 mm.; and e. guide means for mounting a mask in alignment with at least one of said window areas.

13. An optical device in combination with said frame structure according to claim 12 wherein:

a. the mask for each eye is a thin opaque plastic film; and b. said guide means for mounting a mask before each eye includes a raised rib along the top inside part of the frame structure, said rib having a lower surface for engaging the top edge of either one of the plastic film masks, said rib further having a thickness substantially filling the opening between the frame structure and the individual's face when the frame structure is being worn by the individual to block light from entering the individual's eyes through the opening.

14. An optical device in combination with said frame structure according to claim 13 wherein:

a. one film mask is mounted in the frame structure for each of the individual's eyes with the array of one mask disposed out of horizontal alignment with the array of the other mask.

15. An optical device in combination with said frame structure according to claim 13 wherein:

a. said guide means further includes a raised rib along the bottom inside part of the frame structure for aligning the film masks and blocking against light entering the individual's eyes.

16. An optical device in combination with said frame structure according to claim 12 wherein:

each window area further includes a fourth section curved about a horizontal axis and extending from the bottom edge of the first front section inwardly of the frame structure for covering the space between the first section and the individual's cheeks when the frame structure is being worn.

17. An optical device in combination with said frame structure according to claim 16 wherein:

a. the primary array of transparent areas are disposed in alignment with the first, second and third sections of the window area; and b. a secondary array of transparent areas is disposed is alignment with the lower front section and the fourth section of the window area, the transparent areas of said secondary array being spaced closer together than the primary array.

18. An optical device in combination with said frame structure accoording to claim 17 wherein:

a. the primary array on the front, curved and side sections are defined by transparent areas having diameters of about 0.65 mm. and center to center spacings of about 4 mm.

19. An optical device in combination with said frame structure according to claim 18 wherein:

a. the transparent areas of the secondary array have a horizontal center to center spacing of about 4 mm. and a vertical center to center spacing of about 2.5 mm.

20. An optical device in combination with said frame structure according to claim 17 further including:

a. a molded-in lens in the first section of each window area, said lens having a moderate power of between about 2 and 6 diopters.

21. An optical device in combination with said frame structure according to claim 20 wherein:

a. the film masks are secured to the frame structure on the inside surfaces of the window areas; and b. the lens of each window is a planoconvex structure having its convex surface defining the outside surface of the window area.

22. An optical device in combination with said frame structure according to claim 21 wherein:

a. the lens is a 6 diopter lens having a diameter of about 30 mm. and a thickness of about 1 mm.

23. An optical device for use by post-operative cataract patients in combination with means for holding the device in position before the eye, said optical device consisting of:

a. an opaque mask for mounting before the eye, said mask being about 40 × 50 mm. in size;

b. a central array of circular transparent areas in said mask forming a square pattern of about 20 mm. to a side;

c. a side array of transparent areas extending horizontally from the central array toward the outside of the mask, said side array being connected to the central array and having a vertical height of about 9 mm. and horizontal length of about 17 mm.; and d. said transparent areas each having a diameter between 0.375 to 1.0 mm. and being formed on centers spaced from each other in linear rows in parallelogram pattern and together defining about 3% of the surface area of the plate.

24. An optical device according to claim 23 wherein:

a. said transparent areas are spaced on 2.0 mm. to 5.5 mm. centers.

25. An optical device according to claim 24 wherein:

a. said transparent areas are spaced on 4 mm. centers; and b. said transparent areas each have a diameter of 0.5 mm.

26. An optical device according to claim 23 wherein:

a. said array of transparent areas is adjustable horizontally of said mask by a distance at least equal to about one-half the spacing between the transparent areas.

27. An optical device according to claim 23 further including:

a. light blocking means disposed about the periphery of said mask for contact with patient's face to block out all light entering the eye except for that passing through the transparent areas.

* * * * *

UNITED STATES PATENT AND TRADEMARK OFFICE
CERTIFICATE OF CORRECTION

PATENT NO. : 3,967,885
DATED : July 6, 1976
INVENTOR(S) : William H. Byler

It is certified that error appears in the above-identified patent and that said Letters Patent are hereby corrected as shown below:

Column 1, line 50, "apaque" should read --opaque--.

Column 2, line 48, "wrap-aroound" should read --wrap-around--.

Column 5, line 6, "variationsn" should read --variations--;
line 68, "transition of focusing" should read --transition distortion of focusing--.

Column 6, line 38, "cnsidered" should read --considered--.

Column 7, line 39, "eyegless" should read --eyeglass--.

Column 8, line 28, "IN" should read --In--.

Column 9, line 3, "saidd" should read --said--.

Column 10, line 61, "area of the" should read --area of each of the--.

Column 12, line 4, "accoording" should read --according--;
line 24, "planoconvex" should read --plano-convex--.

Signed and Sealed this

Twenty-sixth Day of April 1977

[SEAL]

Attest:

RUTH C. MASON
Attesting Officer

C. MARSHALL DANN
Commissioner of Patents and Trademarks